(12) United States Patent
Davis et al.

(10) Patent No.: US 9,855,014 B2
(45) Date of Patent: Jan. 2, 2018

(54) COMPRESSION PADDLE FOR USE IN BREAST IMAGING

(71) Applicant: GENERAL ELECTRIC COMPANY, Schenectady, NY (US)

(72) Inventors: Cynthia Elizabeth Landberg Davis, Niskayuna, NY (US); Zhipeng Zhang, Santa Clara, CA (US); Weston Blaine Griffin, Niskayuna, NY (US); Ying Mao, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 108 days.

(21) Appl. No.: 14/572,452

(22) Filed: Dec. 16, 2014

(65) Prior Publication Data

US 2016/0166217 A1    Jun. 16, 2016

(51) Int. Cl.
| | | |
|---|---|---|
| *A61B 6/04* | (2006.01) | |
| *A61B 6/00* | (2006.01) | |
| *A61B 6/02* | (2006.01) | |
| *A61B 8/00* | (2006.01) | |

(52) U.S. Cl.
CPC ............ *A61B 6/0414* (2013.01); *A61B 6/025* (2013.01); *A61B 6/4417* (2013.01); *A61B 6/502* (2013.01); *A61B 8/4281* (2013.01); *A61B 8/4416* (2013.01)

(58) Field of Classification Search
CPC .............................. A61B 6/502; A61B 6/0414
See application file for complete search history.

(56) References Cited

U.S. PATENT DOCUMENTS

| | | | |
|---|---|---|---|
| 4,943,986 A | * | 7/1990 | Barbarisi ............... A61B 6/502 378/208 |
| 5,335,257 A | | 8/1994 | Stunberg |
| 5,474,072 A | | 12/1995 | Shmulewitz |
| 5,775,337 A | * | 7/1998 | Hauger ............... A61B 6/0421 128/869 |
| 5,787,522 A | | 8/1998 | Swihart |
| 5,840,022 A | | 11/1998 | Richter |
| 5,938,613 A | | 8/1999 | Shmulewitz |
| 6,102,866 A | | 8/2000 | Nields et al. |
| 6,574,499 B1 | | 6/2003 | Dines et al. |
| 6,846,289 B2 | | 1/2005 | Besson et al. |
| 6,975,701 B2 | | 12/2005 | Galkin |
| 7,349,521 B2 | | 3/2008 | Al-Khalidy et al. |

(Continued)

FOREIGN PATENT DOCUMENTS

| | | |
|---|---|---|
| WO | 9802094 A1 | 1/1998 |
| WO | 2013171671 A1 | 11/2013 |

OTHER PUBLICATIONS

Saunders et al., "The effect of breast compression on mass conspicuity in digital mammography.", Med Phys., pp. 4464-4473, vol. 35, Issue 10, Oct. 2008.

(Continued)

*Primary Examiner* — Hoon Song
(74) *Attorney, Agent, or Firm* — Pabitra K. Chakrabarti

(57) ABSTRACT

The present disclosure relates to the manufacture and use of a non-rigid breast compression paddle, such as a compression paddle having a mesh material forming the primary interface with patient tissue. In certain implementations, an automatic feedback driven approach may be used in conjunction with such a compression paddle for compressing breast tissue.

23 Claims, 11 Drawing Sheets

(56) References Cited

U.S. PATENT DOCUMENTS

| | | | |
|---|---|---|---|
| 7,489,761 | B2 | 2/2009 | Defreitas et al. |
| 7,556,602 | B2 | 7/2009 | Wang et al. |
| 7,656,993 | B2 | 2/2010 | Hoernig |
| 7,742,558 | B2 | 6/2010 | Mertelmeier et al. |
| 7,822,457 | B2 | 10/2010 | Lokhandwalla et al. |
| 7,849,761 | B2 | 12/2010 | Forslund |
| 7,916,918 | B2 | 3/2011 | Suri et al. |
| 8,192,361 | B2 | 6/2012 | Sendai |
| 8,592,772 | B2 | 11/2013 | Stein et al. |
| 2003/0149364 | A1 | 8/2003 | Kapur et al. |
| 2004/0181152 | A1 | 9/2004 | Zhang et al. |
| 2005/0089205 | A1 | 4/2005 | Kapur et al. |
| 2005/0265518 | A1 | 12/2005 | Aubel |
| 2009/0129556 | A1* | 5/2009 | Ahn ................. A61B 6/04 378/208 |
| 2009/0175408 | A1* | 7/2009 | Goodsitt .......... A61B 6/0414 378/37 |
| 2011/0087098 | A1 | 4/2011 | Fischer et al. |
| 2012/0029344 | A1 | 2/2012 | Nakayama |
| 2012/0150034 | A1 | 6/2012 | Defreitas et al. |
| 2013/0116570 | A1 | 5/2013 | Carson et al. |
| 2013/0129039 | A1 | 5/2013 | Defreitas et al. |
| 2014/0121520 | A1 | 5/2014 | Wang et al. |
| 2014/0135623 | A1 | 5/2014 | Manak et al. |
| 2014/0180082 | A1 | 6/2014 | Evans et al. |

OTHER PUBLICATIONS

Sinha et al.,"Multi-Modality 3D Breast Imaging With X-Ray Tomosynthesis and Automated Ultrasound", Conference Proceedings IEEE Engineering Medicine and Biology Society, pp. 1335-1138, Aug. 23-26, 2007.

Kapur et al., "Combination of Digital Mammography With Semi-Automated 3D Breast Ultrasound", Technology in Cancer Research & Treatment, vol. No. 3, Issue no. 4, pp. 325-334, Aug. 16, 2010.

"Frost & Sullivan: Multi-modality Breast Imaging Systems Spur Innovation in Europe", ITN Online, pp. 1-13, Aug. 27, 2014.

PCT Additional search fees issued in connection with corresponding PCT Application No. PCT I US2015/060284 on Feb. 9, 2016.

"Auisition/US Surgical Acquires sonopsy manufacturer NeoVision for $40mm", Pharma Intelligence, https:I/www.pharmamedtechbi.com/deals/19971 0172, pp. 1-4, Mar. 21,2016.

"Tyco Acquires US Surgical for $3.3bn in a stock swap", Pharma Intelligence, https:I/www.pharmamedtechbi.com/deals/199810055, pp. 1-4, Mar. 21, 2016.

PCT Search Report and Written Opinion issued in connection with Related PCT Application No. PCT/US2015/060284 dated Apr. 18, 2016.

U.S. Non-Final Office Action issued in connection with Related U.S. Appl. No. 14/572,416 dated Oct. 19, 2016.

U.S. Final Office Action issued in connection with Related U.S. Appl. No. 14/572,416 dated May 19, 2017.

* cited by examiner

COMPRESSION PADDLE FOR USE IN BREAST IMAGING

BACKGROUND

The present approach relates generally to the field of breast imaging and, more specifically, to compression paddles for use in acquiring breast images.

In modern healthcare facilities, non-invasive imaging approaches are used for identifying, diagnosing, and treating diseases. One purpose to which such techniques are applied is the acquisition of mammographic images for use in identifying and diagnosing lesions or irregularities in the breast tissue.

In conventional approaches, breast imaging or mammography may be implemented using radiographic techniques, such as by projecting X-rays through the breast tissue and reconstructing images based on the differential transmission of the X-rays through the tissue. Such approaches, however, may suffer from various detriments. For example, in such approaches the breast tissue is typically compressed to a substantially uniform thickness so that the X-rays, at all points of interest, are traversing roughly the same thickness of tissue, thereby facilitating analysis. However, such compression can be uncomfortable for the patient. Alternative compression techniques that are suitable for use with appropriate imaging technologies may, therefore, be desirable

BRIEF DESCRIPTION

In one embodiment, a breast compression paddle is provided. The breast compression paddle includes a frame defining an open region and a mesh material affixed to the frame over the open region. The mesh material is deformable relative to the frame.

In a further embodiment, a method is provided for compressing a breast. The method includes the step of automatically lowering a compression paddle onto breast tissue. One or more measurements are acquired indicative of a force measured at the compression paddle. The one or more measurements are compared to one or more threshold compression criteria. If the threshold compression criteria are not met, the compression paddle is lowered further. If the threshold compression criteria are met, further compression by the compression paddle is stopped. The breast tissue is held under compression for the duration of one or more image acquisitions. After completion of the one or more image acquisitions, compression of the breast tissue is released.

In an additional embodiment, a method for manufacturing a breast compression paddle is provided. The method includes the step of applying a mesh material over an open region of a paddle frame. In one implementation, a displacement is applied to the mesh material in at least a first direction. The mesh material, with the applied displacement, is affixed to the paddle frame to produce the breast compression paddle.

In another embodiment, a method for manufacturing a breast compression paddle is provided. The method includes the steps of cutting a mesh material to a fixed size and of mounting the mesh material over an open region of a paddle frame. A pre-determined tension is applied to the mesh material in at least a first direction. The tension on the mesh material is released and the mesh material is affixed to the paddle frame to produce the breast compression paddle.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present approach is directed towards acquisition of breast image data, such as the acquisition of ultrasound image data. For example, in certain embodiments, an imaging system may be used to implement a pre-programmed scan protocol in an automated manner. Such scan protocols may involve compression of the breast tissue but, in certain embodiments, such compression need not involve compressing the breast tissue to uniform thickness (i.e., the compression may be tapered or angled so as to accommodate the patient anatomy. Further in some embodiments, the compression paddles employed may be at least partly conformable.

In certain embodiments discussed herein, the compression paddle may be used in conjunction with a suitable imaging modality or combination of modalities, such as ultrasound and/or tomosynthesis. In certain examples discussed herein, the compression paddles may be described in use with a combined tomosynthesis/ultrasound imaging system, with a tomosynthesis imaging system, or with an ultrasound imaging system. While the present compression paddle may be useful in conjunction with such modalities (alone or in combination), it should be appreciated that such examples are provided merely to facilitate explanation, and are not intended to represent the only types of imaging modalities that might benefit from the use of the presently described paddles or methodologies. Indeed, the present paddles may be employed with any suitable imaging modality where compression of the breast tissue is employed, but where such compression need not result in uniform or near uniform thickness of the compressed tissue and/or where conformity to the breast tissue may be desirable.

Figure 1:
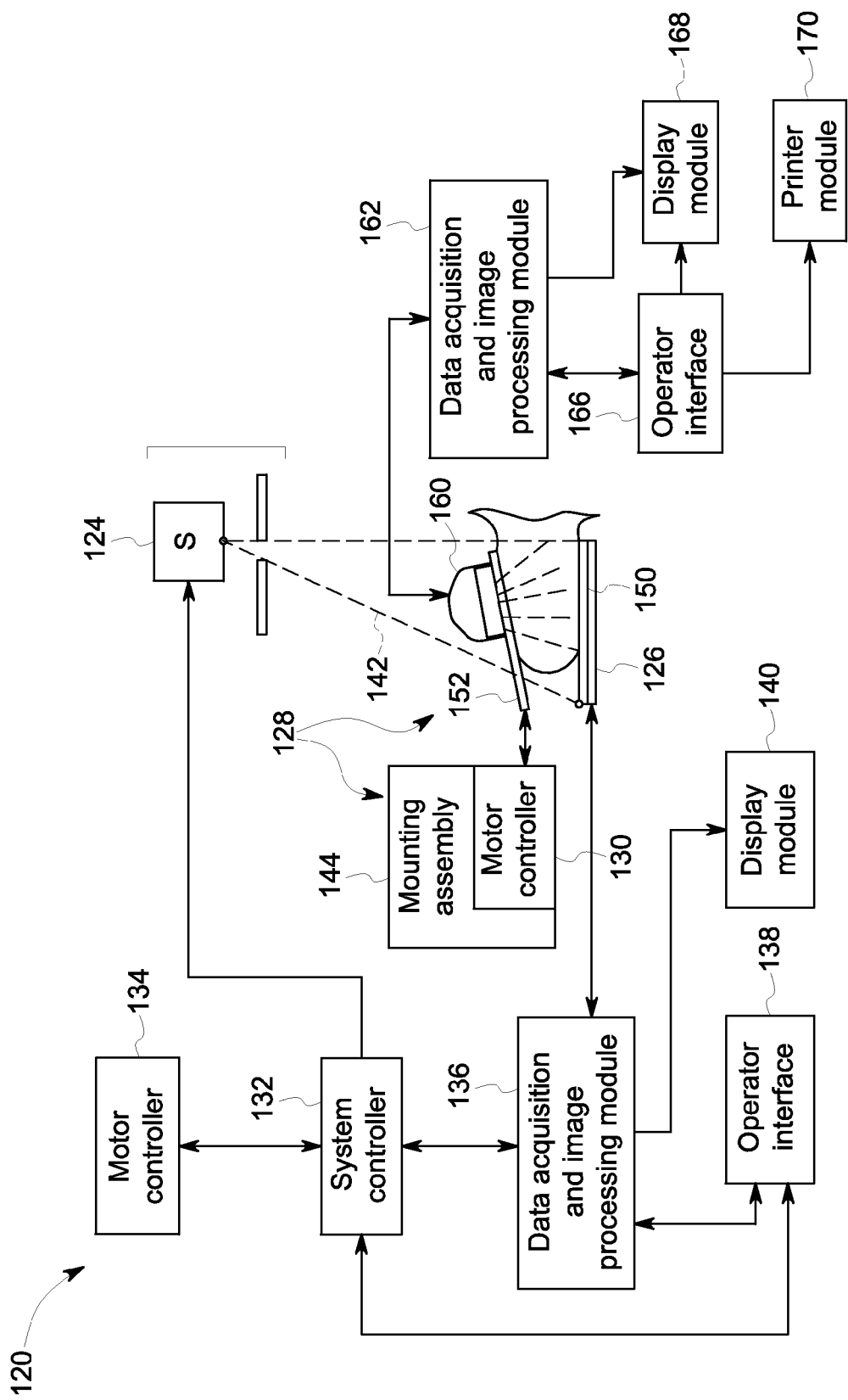
FIG. 1 is a diagrammatic representation of one embodiment of a multi-modality breast imaging system in accordance with aspects of the present disclosure.

With this in mind and turning to FIG. 1, an example of a combined, multi-modality imaging system 120 (including both tomosynthesis and ultrasound components) is depicted which may utilize a compression paddle and compression approach as discussed herein. As noted above, the present discussion related to multi-modality implementations is provided merely to facilitate explanation. The compression paddle and compression approaches discussed herein may also be suitable for single modality implementations, whether with a tomosynthesis system, ultrasound system, or other suitable modality.

As depicted, the imaging system 120 includes a tomosynthesis image data acquisition subsystem for acquiring tomographic image data. The tomosynthesis imaging subsystem includes an X-ray source 124, an X-ray detector 126 and a compression mechanism 128 that may be used to position the patient tissue and to generate signals representative of X-ray transmission through the tissue of interest. In the depicted example, the compression mechanism 128 includes a variety of components, such as a mounting assembly 144, a motor controller 130, a lower compression plate 150, and an upper compression plate or paddle 152. The tomosynthesis imaging subsystem further includes a system controller 132, a motor controller 134, data acquisition and image-processing module 136, an operator interface 138 and a display module 140.

The X-ray source 124 may, in certain implementations, include an X-ray tube (or other suitable X-ray generating mechanism) and a collimator configured to generate a beam of X-rays 142 when active. In an implementation of a tomosynthesis imaging system, the X-ray source 124 is movable in a one, two or three dimensional trajectory relative to the volume being imaged (such as along a line or a curve) such that the X-ray source moves over a limited angular range relative to the volume being imaged. Movement of the X-ray source may be manual, automated, or some combination (e.g., manual initial positioning with automated movement during scanning).

The X-ray detector 126 may be stationary, or may be configured to move either independently or in synchrony with the X-ray source 124. In a breast imaging embodiment, the X-ray detector 126 may be positioned proximate to and beneath the breast tissue of the patient, and thus may be incorporated as part of or proximate to the compression mechanism 128. For example, the X-ray detector 126 may be disposed immediately or proximately beneath a bottom plate of compression mechanism 128 such that the breast tissue does not rest directly on the detector 126 but on a plate or other compression support above the detector 126.

In certain breast imaging embodiments, the compression mechanism 128 (i.e., the aggregation of the mount 144, motor controller 130, and compression plates or paddles 150, 152) is configured to compress the breast tissue during both tomosynthesis and ultrasound image acquisitions, i.e., a single compression for both imaging scans. For example, in one such embodiment, the compression mechanism 128 may include a motor controller 130 configured to move at least on compression paddle 152 in response to a control or feedback scheme to apply a specified compression to the breast tissue. In the depicted example a double-headed arrow is shown to denote not only that the motor controller 130 may provide force and/or control signals to the paddle 152, but also that control or feedback signals may be received by the controller from the paddle 152 during operation, such as from one or more electrical or mechanical sensing devices on the paddle 152. In operation, the compression mechanism 128 may be used to stabilize and immobilize the imaged breast tissue during acquisition of both the tomosynthesis and the ultrasound datasets and to maintain uniformity of the tissue both during and between image acquisitions. Thus, in practice, at least part of the compression structures of the assembly 128 may transmit X-rays (i.e., may be radiolucent) for the tomosynthesis image acquisition) and may transmit the ultrasound signals (i.e., may be sonolucent) for the ultrasound image acquisition. As noted above, in one embodiment, the compression mechanism 128 includes a lower plate 150, (such as a flat, inflexible plate) on which the breast tissue may rest, and an upper plate or paddle 152 which lowers onto the breast tissue to effect compression. In one implementation, the upper paddle 152 is non-rigid over all or part of its surface. For example an embodiment of the upper paddle 152 may be at least partly formed using a flexible, non-rigid mesh material (i.e., formed as a mesh paddle) that is both radiolucent and sonolucent and which is at least partially conformable to the shape and size of the breast tissue.

In a tomosynthesis implementation, and unlike conventional radiographic mammography techniques, it is not necessary for the breast tissue to be compressed to a substantially uniform thickness. That is, due to the nature of the tomosynthesis image acquisition process, the breast tissue need not be of uniform thickness in order to generate useful diagnostic images. Likewise, the ultrasound image acquisition does not require that the breast tissue be of uniform thickness. Thus, in certain embodiments the upper compression paddle 152 may rotate or approach the lower plate 150 at an angle such that, when engaged, the paddles or plates 150, 152 are not parallel to one another but, instead, remain at an angle with respect to one another. This angle can be such that the chest wall side is higher for imaging of a cranial caudal (CC) view, for example, or where the left or right side is higher for a medial lateral oblique (MLO) view. Such accommodative compression may reduce patient discomfort by at least partly conforming to the shape of the breast tissue. In addition, as discussed in greater detail below, the compression paddle 152 may be constructed to be non-rigid or flexible, at least in part, such as by using suitable non-rigid materials (e.g., mesh).

In the depicted implementation, the system controller 132 controls operation of the tomosynthesis imaging subsystem and provides for any physical motion of the X-ray source 124 and/or the X-ray detector 126. In the depicted embodiment, mechanical movement of the imaging components is effected via the motor controller 134 in accordance with a prescribed imaging trajectory for use in tomosynthesis. Therefore, by means of the tomosynthesis imaging subsystem, the system controller 132 may facilitate acquisition of radiographic projections at various views along a limited angular range relative to a patient. In general, the system controller 132 commands operation of the tomosynthesis imaging system 120 to execute examination protocols and to acquire resulting data.

In one implementation, the tomosynthesis data acquisition and image-processing module 136 communicates with the X-ray detector 126 and typically receives data from the X-ray detector 126, such as a plurality of sampled analog signals or digitized signals resulting from exposure of the X-ray detector to X-rays. The tomosynthesis data acquisition and image-processing module 136 may convert the data to digital signals suitable for processing and/or may process sampled digital and/or analog signals to generate volumetric images of the breast tissue which may, in turn, be displayed on the display module 140.

The operator interface 138 can be used to customize settings for the tomosynthesis imaging and for effecting system level configuration changes as well as for allowing operator activation and operation of the tomosynthesis imaging system 120. In the depicted embodiment, the operator interface 138 is connected to the system controller 132, image-processing module 136, and the display module 140.

Shown in conjunction with the tomosynthesis imaging subsystem components discussed above are ultrasound imaging system components that may be present in a combined (i.e., multi-modality) system. In the depicted example, the ultrasound imaging subsystem includes an ultrasound probe 160, an ultrasound data acquisition and image-processing module 162, which includes beam-formers and image reconstruction and processing circuitry, an operator interface 166, a display module 168 and a printer module 170. In a multi-modality imaging system based upon both X-ray and ultrasound techniques, certain of these components or modules may be partially or fully integrated to perform image acquisition and processing for both systems. Alternatively, in other implementations, both the X-ray and ultrasound subsystems may be largely autonomous from one another, with separate user workstations or interfaces as well as separate scan subsystems.

In certain embodiments, the ultrasound imaging subsystem uses the ultrasound probe 160 for transmitting a plurality of ultrasound signals into an object, such as the breast tissue of a patient being imaged, and for receiving a plurality of reflected ultrasound signals from the tissue. In certain implementations, the ultrasound imaging subsystem may employ beam steering techniques to help image all areas of the breast tissue. The reflected ultrasound signals from the tissue convey information about thickness, size, and location of various tissues, organs, tumors, and anatomical structures in relation to transmitted ultrasound signals. The plurality of reflected ultrasound signals received by the ultrasound probe 160 are processed for constructing an image of the object.

In certain embodiments, movement and operation of the ultrasound probe 160 is automated. In these embodiments, the ultrasound probe 160 may be manually or automatically brought into contact with the tissue being imaged or with the overlying sonolucent paddle structure 152 compressing the breast tissue. The ultrasound probe 160 may then be moved via a mechanical subsystem to move with respect to the breast tissue while acquiring ultrasound image data. In some embodiments, upon completion of the prescribed acquisition protocol, one or both of the ultrasound probe 160 or the paddle 152 may be automatically disengaged from the tissue. In certain implementations, the ultrasound probe 160, and any radiopaque supporting structures, are removed from the X-ray beam path when a tomosynthesis examination is being performed or, more generally, when an ultrasound examination is not being performed.

The ultrasound data acquisition and image-processing module 162 sends signals to and receives information from the ultrasound probe 160 during an imaging procedure. Thus, the ultrasound data acquisition and image-processing module 162 may control the strength, beam focus or forming, duration, phase, and frequency of the ultrasound signals transmitted by the ultrasound probe 160, and may decode the information contained in the plurality of reflected ultrasound signals from the tissue to a plurality of discernable electrical and electronic signals. Once the information is obtained, an ultrasound image of the object located within a region of interest is reconstructed in accordance with generally known reconstruction techniques.

The operator interface 166 may include a keyboard, a mouse, and other user interaction devices. The operator interface 166 can be used to customize a plurality of settings for an ultrasound examination (including settings related to the automated operation of the probe 160), to effect system level configuration changes, and to allow operator activation and operation of the ultrasound imaging system 32. The operator interface 166 is connected to the ultrasound data acquisition and image-processing module 162, the display module 168 and to the printer module 170. The display module 168 receives image information from the ultrasound data acquisition and image-processing module 162 and presents the image of the object within the region of interest of the ultrasound probe 160. The printer module 170 is used to produce a hard copy of the ultrasound image in either gray-scale or color. As noted above, some or all of these system components may be integrated with those of the tomosynthesis X-ray system described above.

Figure 2:
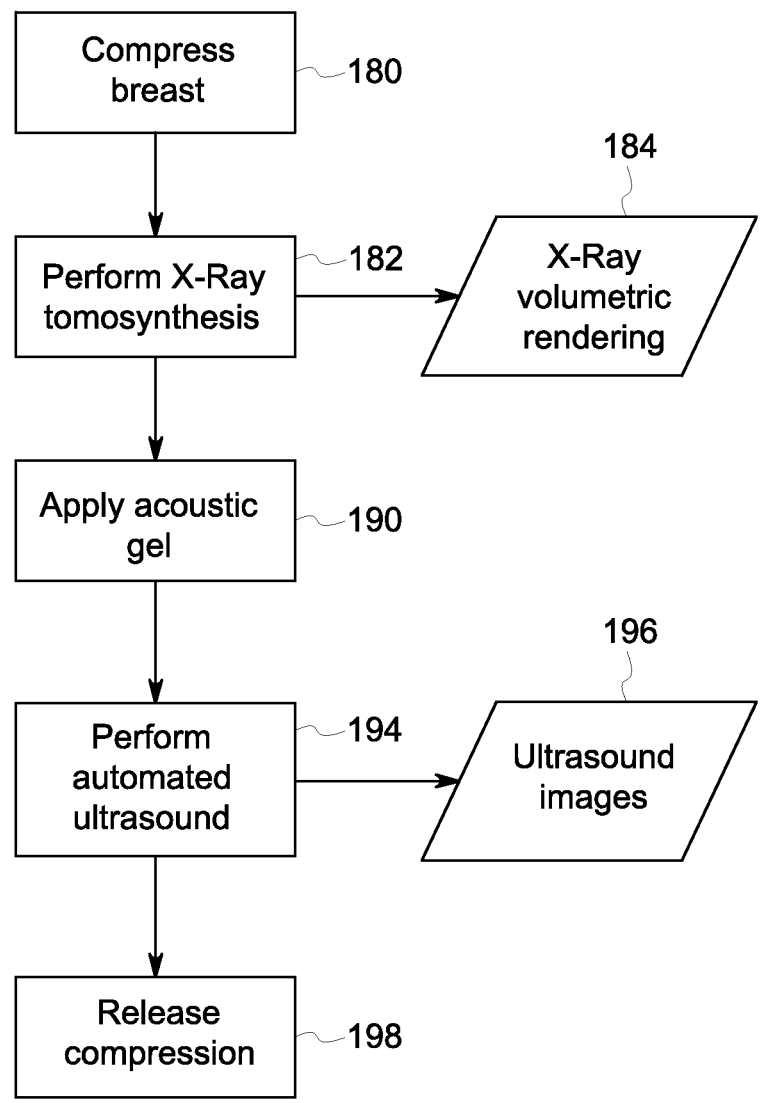
FIG. 2 is a process flow diagram of a combined tomosynthesis and ultrasound image acquisition, in accordance with aspects of the present disclosure.

Turning now to FIG. 2, an example of a process flow of one implementation of a scan session employing a compression paddle as discussed herein is illustrated in a flow chart. In this example, the breast tissue is initially compressed (block 180) to the desired thickness or range of thickness. As noted above, unlike conventional radiographic mammography approaches, the compression need not result in a uniform thickness of tissue being imaged and may instead be more accommodative of the breast shape by allowing a tapered or angled compression. In addition, the compression may be performed using a non-rigid paddle structure 152, such as a mesh paddle structure, that is accommodative or conformable to the breast tissue size and shape.

In certain embodiments where a non-rigid paddle 152 is employed, conventional force and distance approaches may not be suitable for determining the effective compression on the breast tissue. Instead, in such embodiments, various force measurement and feedback approaches, as discussed herein, may be employed. For example, compression force feedback or other approaches may be used to determine when the motion of the compression paddle 152 is stopped, i.e., when sufficient contact is established. For example, in one embodiment, compression of the breast tissue is stopped based upon specified or derived threshold criterion. In some embodiments, the change in force per unit distance moved by the paddle may be measured and monitored and, based upon this measure a determination may be made as to when compression is to be stopped (i.e., when a threshold force per distance value is reached). For example, compression may continue in certain implementations to a certain specified force or to a threshold point where the increase in achieved compression is reduced or negligible in view of the additional applied force.

In certain embodiments, one or more sensors (such as strain sensors provided on the edge of the paddle 152 or at the paddle mount on compression mechanism 128) may be monitored for an indication that the desired force threshold is reached, stopping compression. In other embodiments, the electrical properties of a wire or wires woven through a mesh material of the paddle 152 may be monitored and used to determine the force per unit area or force per unit distance moved, which may then be compared to a threshold.

In one embodiment, the respective threshold used to evaluate when compression is sufficient may be based on values queried from a look-up table or determined from on-the-fly calculations. For example, in a look-up table embodiment, a table of compression force and thickness curves may be accessible to the system (such as stored on the system or on an accessible network location). Different curves may be provided for different sizes and types of paddles 152, and/or for different patient variable such as age, body mass index, breast or cup size, breast density, and so forth. As will be appreciated, different, interchangeable paddles may also be provided based on these factors or on combinations of these factors. Based on these examination specific factors, the appropriate curves may be queried to provide the correct compression threshold values. In such embodiments, the force sensors may provide measures of the trajectory of the paddle 152 on the breast and consultation with the appropriate table or curves may be used to establish when the curve is optimized. In certain embodiments, the system may reduce compression by some nominal amount once the compression threshold is reached (e.g., by 1 mm or less) to improve patient comfort and to allow for any overshoot by the compression mechanism.

In the depicted example, an X-ray tomosynthesis is performed (block 182) on the compressed breast tissue and a resulting volumetric rendering 184 is generated. In certain implementations, an acoustic coupling gel or lotion may be applied (block 190) prior to ultrasound imaging. In embodiments employing a mesh compression paddle 152, the mesh structure allows passage of the acoustic gel to facilitate acoustic coupling of the probe 160 through the paddle 152 and with the breast tissue. In the depicted example, an automated ultrasound scan is performed (block 194) and ultrasound imaged 196 generated. Upon completion of the scan, compression may be released (block 198) or reduced.

Figure 3:
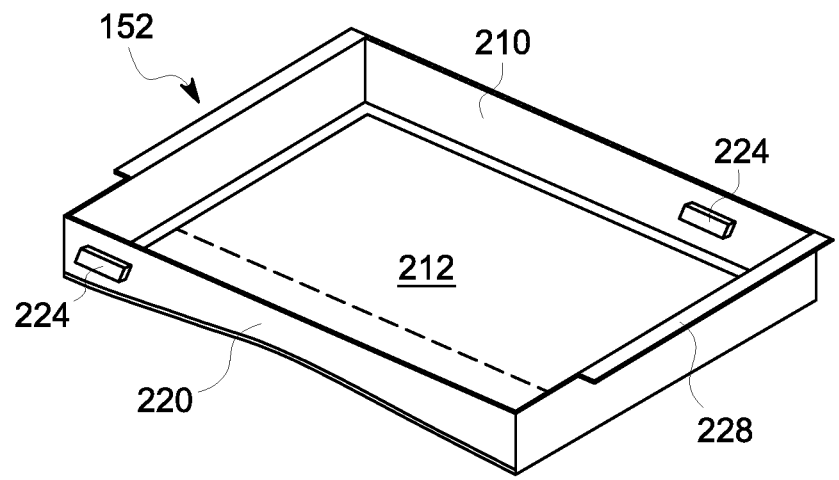
FIG. 3 depicts a non-rigid compression paddle, in accordance with aspects of the present disclosure.
Figure 4:
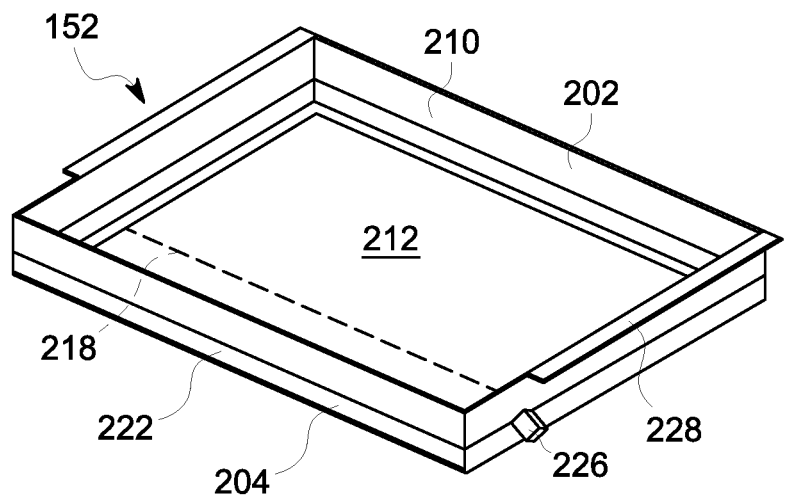
FIG. 4 depicts a non-rigid compression paddle, in accordance with further aspects of the present disclosure.

With the preceding discussion in mind, FIGS. 3 and 4 each depict examples of a compression paddle 152 in accordance with aspects of the present disclosure. In each example, the paddle 152 includes a frame 210 defining the overall shape of the paddle 152 and conveying sufficient stiffness to allow compression of the breast tissue in operation. For example, the frame 210 may be formed from a variety of suitable materials including, but not limited to, plastics or polymers (e.g., engineering plastic), metal or metal alloys, ceramics, and/or composites. In addition, the embodiments of FIGS. 3 and 4 depict a cutout region of the paddle over which a mesh material 212 (such as a polyester mesh material) is affixed, either loosely or under tension. In one embodiment, the mesh material 212 may be of uniform (i.e., constant) tension across the cutout region in one or two directions. In other embodiments, the mesh material 212 may be at different tensions at different points within the cutout region. For example, the tension of the mesh material 212 may increase or decrease in the direction approaching the chest wall relative to other portions of the paddle 152. Thus, the tension of the mesh material 212, if not constant across the cutout region, may vary along one or both of the major or minor axis (i.e., length or width) of the paddle 152 in whatever manner is needed to apply the desired degree of compression to the breast tissue using a given paddle 152.

Likewise, the composition and curvature of a given paddle may be selected so as to provide the desired compression and comfort when using a given paddle, for example, FIG. 3 depicts a paddle 152 having a curved chest wall beam 220. In such a curved embodiment, the curvature may run the length and/or width of the paddle or may taper off. Likewise, the degree or extent of curvature may change over the curved region, such as to accommodate a patient's anatomy or the shape of an imaging component, such as an ultrasound probe head, or the imaging view to be performed. That is, in one embodiment the paddle 152 may be curved so as to correspond to the curvature of an imaging component, such as an ultrasound probe. Conversely, the paddle 152 of FIG. 4 is depicted as having a flat chest wall beam 222 across its length.

It should also be noted that all or part of the paddle 152 may be constructed to be disposable. For example, turning to FIGS. 3 and 4, the paddle 152 of FIG. 3 is shown as being constructed as one piece and, thus, depending on the cost and manufacture of this single-piece construction may be intended for a single-use or limited number of uses (i.e., disposable) or for general reuse, such as with routine cleaning and maintenance (i.e., reusable). Conversely, the paddle 152 of FIG. 4 is shown as being a multi-piece construction, in this example having a reusable paddle portion 202 and a disposable mesh and frame portion 204. In one implementation, the disposable mesh and frame portion 204 can be removably attached to the reusable paddle portion 202, such as using magnetic or mechanical fasteners. In this manner, the mesh and frame portion 204 can be disposed of after a single or limited number of uses while the paddle portion 202 can continue to be used with a new mesh and frame portion 204.

In some embodiments, an X-ray opaque or attenuating material (e.g., thread or line) may be woven into the mesh material 212 or the mesh material may be constructed such that one or more of the constituent lines are sufficiently radio-opaque (such as formed at a thicker gauge) so as to show on radiographic images, including tomosynthesis images. In such embodiments, the subset of radio-opaque lines may be discerned in the images and used to determine the contour or shape of the breast during the image acquisition process. In such an implementation, the contour or shape information determined from the subset of interwoven radio-opaque lines may be used in the tomosynthesis reconstruction process and image presentation.

In certain embodiments the chest wall edge of the paddle 152 may include a loose edge or be provided with some degree of gripping ability such that, when positioned on the patient, the patient tissue is pulled inward with respect to the paddle 152. In a paddle designed specifically for the CC (cranial caudal) view the chest wall edge of the paddle may be taller and more rigid than the far side of the paddle to exert greater force on the pectoral muscle and better enable the inclusion of the most breast tissue in the view. In a paddle designed specifically for the MLO (medial lateral oblique view) the chest wall edge of the paddle and sides may be shorter and more flexible to allow for easier positioning around the shoulder. In addition, in certain embodiments, the paddle 152 (or an associated or attached component may include a wrap or strap that may extend partly or completely around the torso of the patient so as to affix the paddle to the chest wall of the patient during use.

FIGS. 3 and 4 each also depict force or strain sensing mechanisms that may be used during operation to provide compression feedback that may be used in controlling the amount of compression applied by the paddle 152. For example, turning to FIG. 3, a pair of force sensors 224 or strain gauges are provided on surfaces of the paddle 152 which may be used to measure force or strain at different points on the paddle 152, to generate signals corresponding to the measured force or strain, and to communicate such signals to a control component of the compression mechanism 128, such as to motor controller 130. Similarly, FIG. 4 depicts an alternative sensing embodiment in which a conductive wire 218 is woven through the mesh 212 and interrogated by electrical sensing components 226, which measure and report an electrical property of interest of the wire 218. Measurements of the electrical property of interest or changes in the measured property of interest maybe used to determine force or strain along the surface of the compression paddle 152. More generally, any pressure or tension sensing approach may be used, including implementations that don't utilize measuring the electrical properties of conductive wire. Examples of other pressure or tension sensing approaches that may be employed include, but are not limited to, use of piezoelectric materials, capacitive sensors, or optical fibers The paddles of FIGS. 3 and 4 are also depicted as having a flange 228 for fitting a sliding engagement, as discussed below with respect to FIG. 5. In particular, the paddles 152 may be made to be interchangeable such that a suitable paddle may be selected and fitted for a given patient based upon the patient's age, body mass index, breast or cup size, breast density, and so forth as well as the imaging view to be performed (cranial caudal or medial lateral oblique and so forth) For example, in one embodiment (turning to FIG. 5), a paddle 152 may be slid in and out of a larger paddle holder 230 via a sliding engagement that engages the flange 228 (e.g., an engagement of flange 228 with slot 232). In this manner, a paddle 152 suitable for use with a given patient may be inserted into (or removed from) the paddle holder 230 as needed. In the depicted example, the paddle holder 230 includes an ultrasound probe head 236 configured to travel along the compression assembly and interface with the mesh material 212 to ultrasonically interrogate the compressed tissue. In such an embodiment, the curvature of the paddle 152 may correspond to a curvature of the probe 236.

Figure 5:
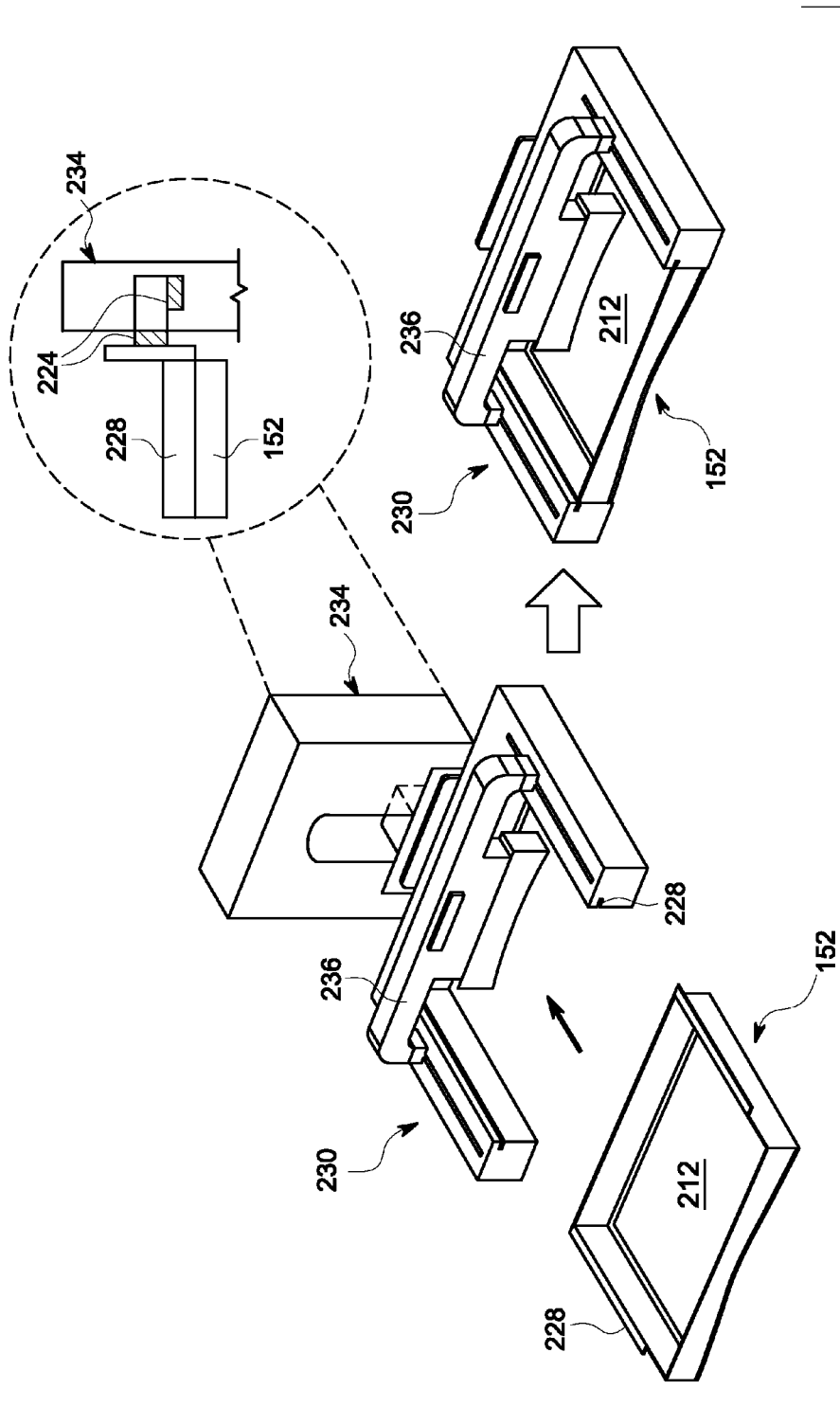
FIG. 5 depicts association of a paddle assembly with an ultrasound scan assembly, in accordance with aspects of the present disclosure.

As depicted in the example, the paddle holder 230 may include or be part of the overall compression mechanism 128 discussed herein, including the depicted compression motor assembly 234, which is configured to move the assembly and engaged paddle up and down so as to engage or disengage the patient tissue. As shown in FIG. 5, in some embodiments the interface between the paddle holder 230 and compression motor assembly 234 may be suitable for positioning one or more force or movement sensors 224, such as strain gauges, as shown in the depicted side profile inset.

Figure 6:
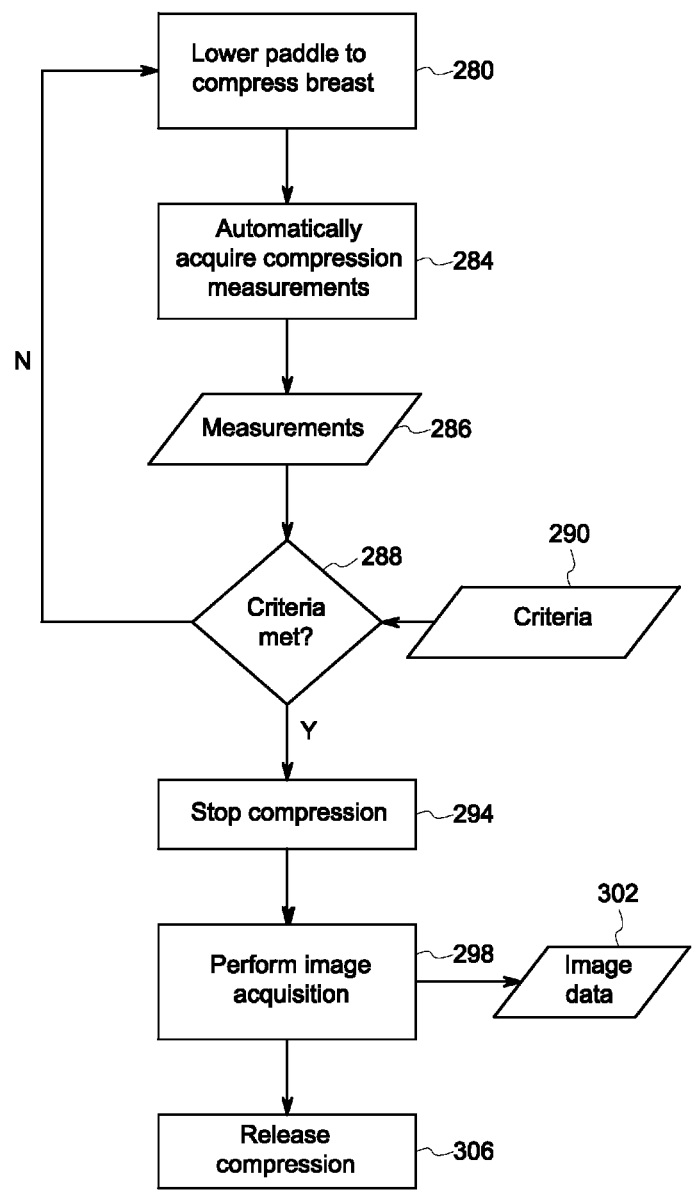
FIG. 6 is a process flow diagram of an automated paddle compression implementation, in accordance with aspects of the present disclosure.

With the preceding discussion in mind, and turning to FIG. 6, a process flow diagram is provided depicting steps in an automated compression step employing a compression paddle. As will be appreciated, the depicted steps may be performed automatically, such as by a programmed controller or processor using a motorized mechanism to move or lower the compression paddle. For example, the compression paddle may be lowered and controlled in response to the initiation of a patient scan or scan protocol. Further, the compression paddle controlled in this manner may be a compression paddle as discussed herein (such as a compression paddle 152 incorporating a mesh material) or a conventional compression paddle design. In addition, the compression approaches discussed herein may be suitable for use with a variety of breast imaging technique including, but not limited to, ultrasound and tomosynthesis techniques.

With this in mind, and turning to FIG. 6, the depicted algorithm is shown as initially lowering (block 280) a compression paddle to compress the breast tissue of a patient undergoing imaging. In the depicted example, one or more compression measurements 286 are automatically acquired (block 284) as compression is applied. Such measurements 286 may be acquired from one or more sensing elements on the compression paddle or mounted between the holder 230 and compression motor assembly 234 (as shown in FIG. 5) and may include measurements of mechanical or electrical properties associated with some portion of the paddle, such as strain or force measured at a point on the paddle or the measurement or change of resistance or impedance in a conductive component of the paddle. By way of example, the measurements may be in the form of direct force-based measurements (e.g., load cell measurements) or indirect deflection measurements (e.g., measures of paddle bending or measures obtained from spring-biased joint having a single degree of freedom).

The measured values 186 may be compared (decision block 288) to a threshold criterion 290 that may be indicative of the desired compression for a given patient. The threshold criterion 290 may be derived on the fly or via querying a local or remote look-up table. The threshold criterion may be based on a variety of factors including, but not limited to, one or more of the patient's age, body mass index, breast or cup size, breast density, and so forth. By way of example, in one embodiment information derived from a prior examination or from the patient's medical records such as breast thickness and density information, may be used as an input to an automatic compression calculation which determines and outputs the optimal breast compression for one or more imaging modalities, such as tomosynthesis and ultrasound. If prior examination is not available other, available information (such as body mass index, cup size, and so forth) may be utilized by such an algorithm to determine the desired compression.

If the threshold criterion 290 is not met by the current measurements 286, the compression paddle may be lowered further. In some embodiments, the rate at which compression is applied may decrease as the target compression threshold is approached. If the criterion 290 is met by the current measurements 286, compression may cease (block 294). In certain embodiments, a technologist may be provided with the capability to continue compression past the point where it would be automatically stopped or, conversely, to cease compression before the threshold criterion is met. In certain embodiments, once the cessation of compression is indicated, the compression paddle may actually be "backed-off" by some nominal amount (e.g., 1 mm) to allow for possible overshoot of the applied compression and/or to provide patient comfort. As noted herein, compression by the present approaches does not have to result in substantially uniform breast thickness and may instead result in a tapered or angled compression profile suitable for use with imaging modalities where uniform compression is not required (e.g., ultrasound, tomosynthesis, and so forth)

Once compression is stopped, breast images 302 may be acquired (block 298) by one or more imaging modalities, such as ultrasound and/or tomosynthesis modalities. In certain embodiments a single compression event may be employed to acquire breast images using multiple imaging modalities, with compression being fully released (block 306) upon completion of imaging by the last modality. In some embodiments where differing imaging modalities may benefit from different degrees of compression, the amount of compression applied may be changed (increased or decreased) between imaging protocols. For example, in a tomosynthesis/ultrasound implementation, an initial compression may be automatically applied followed acquisition of the tomosynthesis image data. Upon completion of the tomosynthesis acquisition, the compression may be reduced or lessened to a level determined to be appropriate for ultrasound imaging (e.g., to a different point on a suitable compression curve selected based on the patient's characteristics). In this manner, patient comfort and ultrasound probe contact may be increased during certain portions of the imaging examination, such as during an ultrasound portion.

Figure 7:
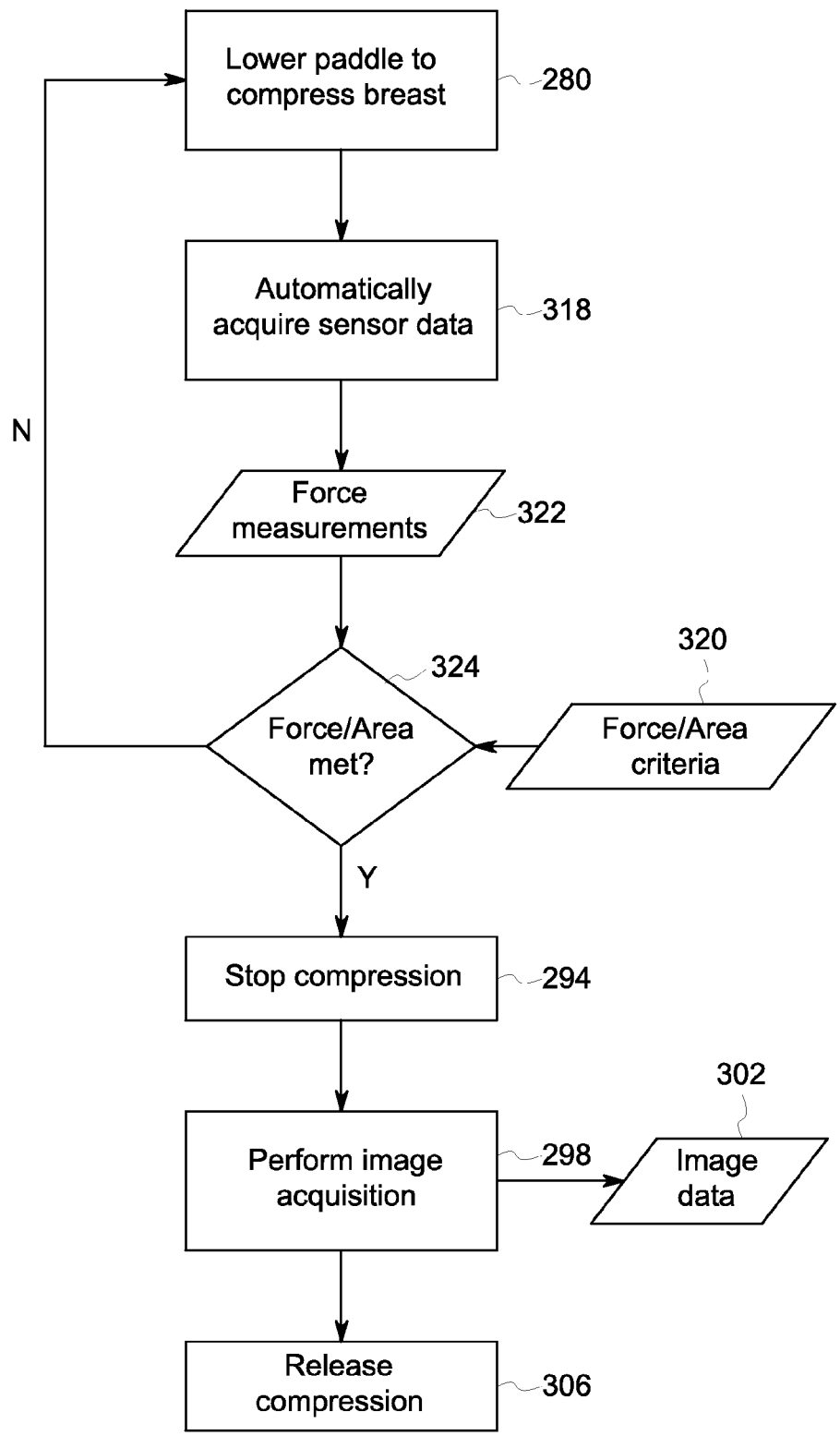
FIG. 7 is a process flow diagram of one implementation of an automated paddle compression implementation, in accordance with aspects of the present disclosure.
Figure 8:
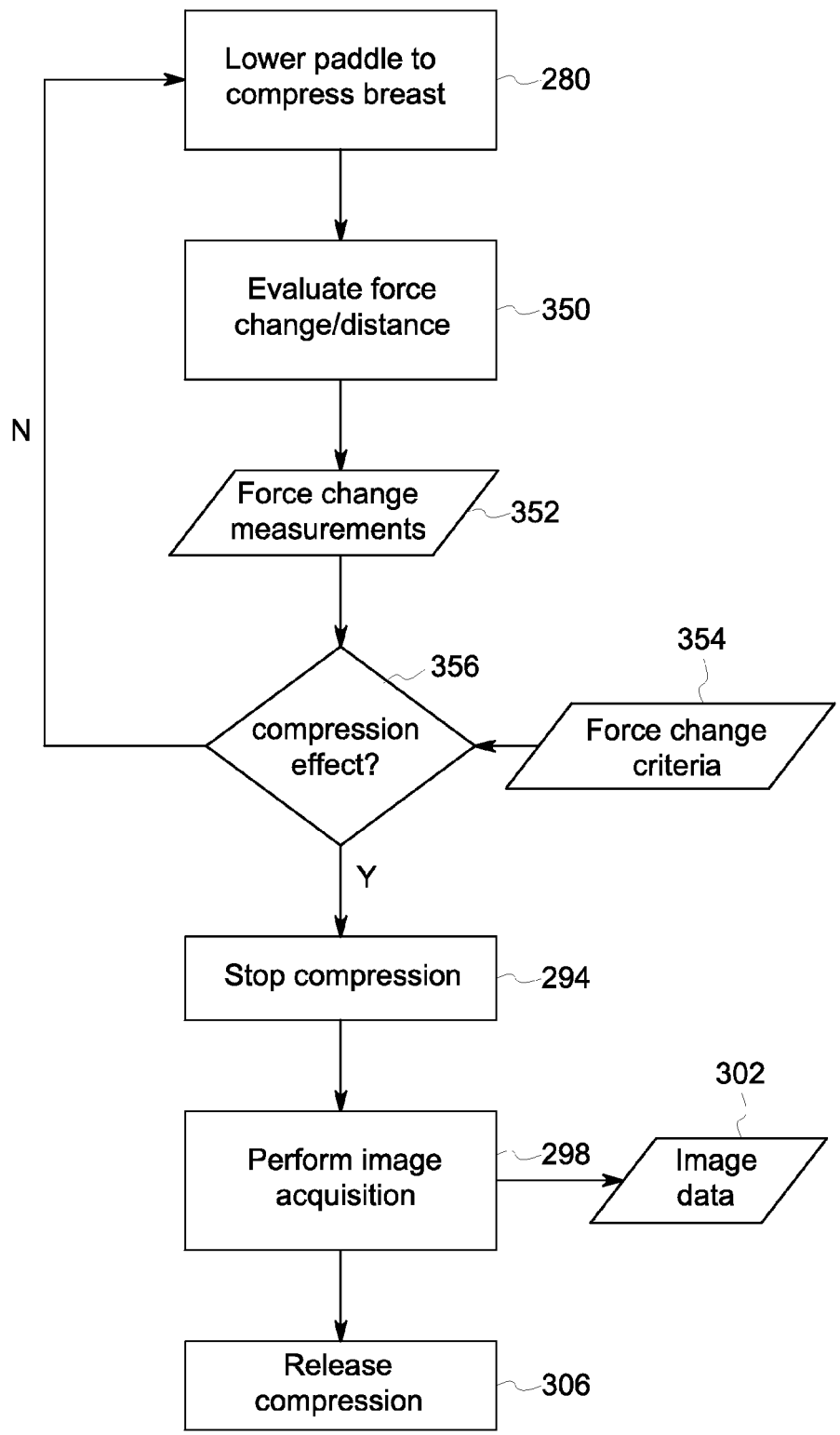
FIG. 8 is a process flow diagram of a further implementation of an automated paddle compression implementation, in accordance with aspects of the present disclosure.

While FIG. 6 describes a generalized compression approach, FIGS. 7 and 8 each provide example of more specific implementations. For example, turning to FIG. 7, in this example, the threshold criterion 320 is compared to a measure 322 of force or force per unit area. In this example, force measurements 322 may be acquired (block 318) during compression, such as from one or more force sensors, strain gauges, or electrical sensors disposed on the compression paddle or mounted between the holder 230 and compression motor assembly 234 (as shown in FIG. 5). Once a determination (block 324) is made that the threshold force or force per area criterion is met, compression is stopped (block 294) and imaging may proceed (block 298), followed by automatic release (block 306) of compression after completion of the imaging sequence.

Turning to FIG. 8, in an alternative implementation, the threshold criterion 354 may be a measure of the change in force as compression is applied. In this example, force change measurements 352 may be acquired (block 350) during compression, such as from one or more force sensors, strain gauges, or electrical sensors disposed on the compression paddle or mounted between the holder 230 and compression motor assembly 234 (as shown in FIG. 5). Once a determination (block 356) is made that the threshold change in force criterion is met, compression is stopped (block 294) and imaging may proceed (block 298), followed by automatic release (block 306) of compression after completion of the imaging sequence.

Figure 9:
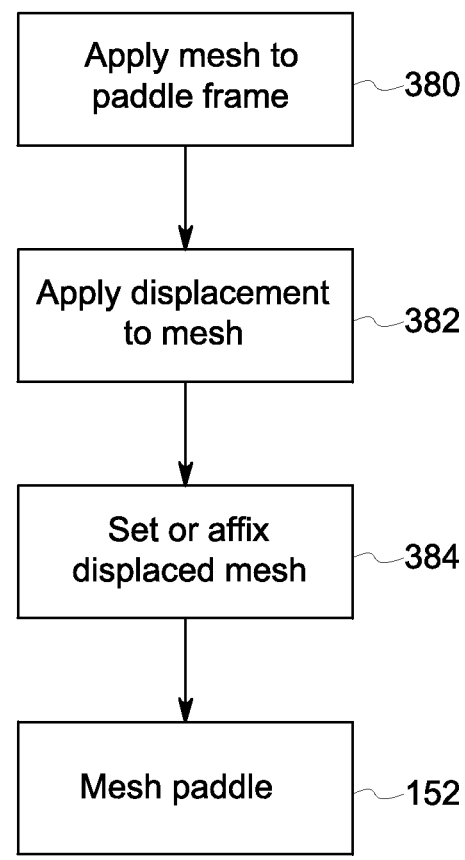
FIG. 9 is a process flow diagram of a manufacturing process for a non-rigid compression paddle, in accordance with aspects of the present disclosure.
Figure 10:
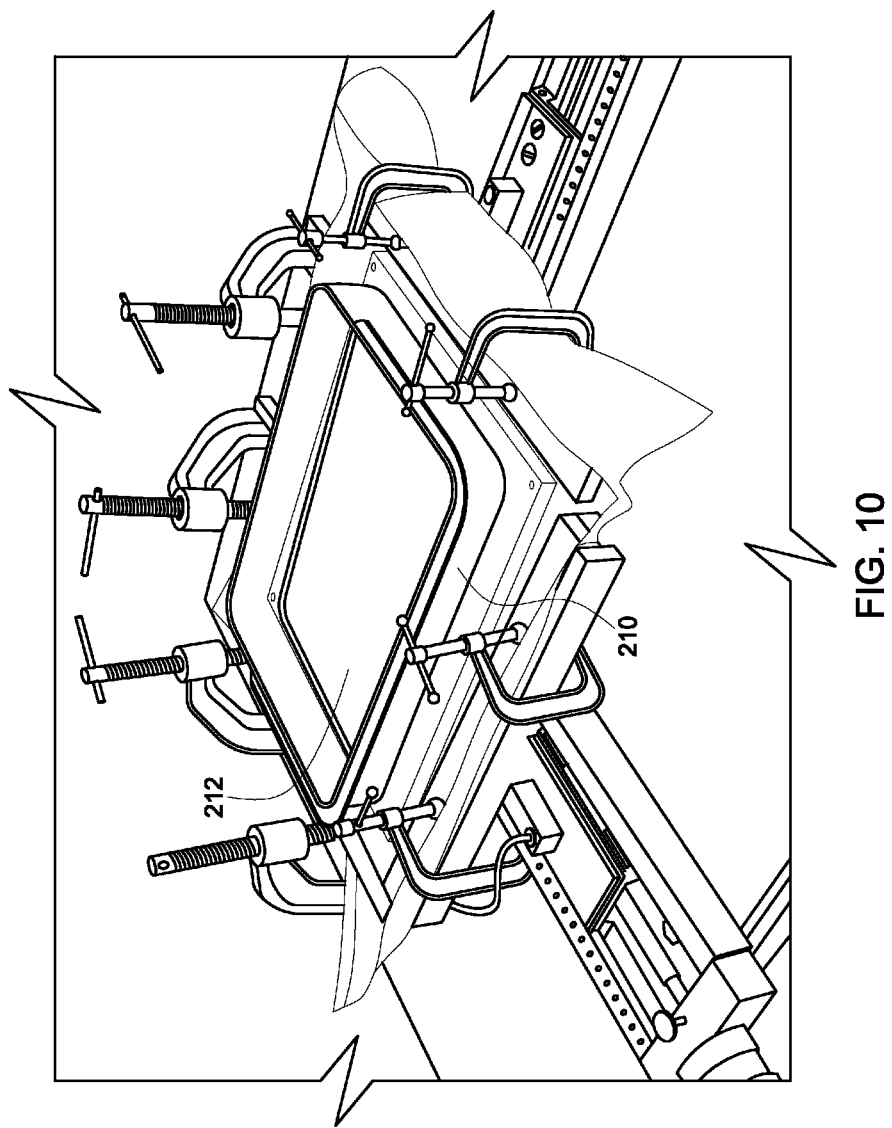
FIG. 10 is a pictorial representation of a paddle form and mesh, in accordance with aspects of the present disclosure.

Turning to FIG. 9, a process flow is depicted for manufacturing a compression paddle in accordance with aspect of the present disclosure. In the depicted example a first step 380 involves applying a mesh material 212 over a frame 210 having an open or cutout region spanned by the mesh. One example of a suitable mesh material is a polyester mesh material, though other mesh materials may instead be employed. As example of a mesh material 212 being applied to an open frame 210 is shown in FIG. 10.

Figure 11:
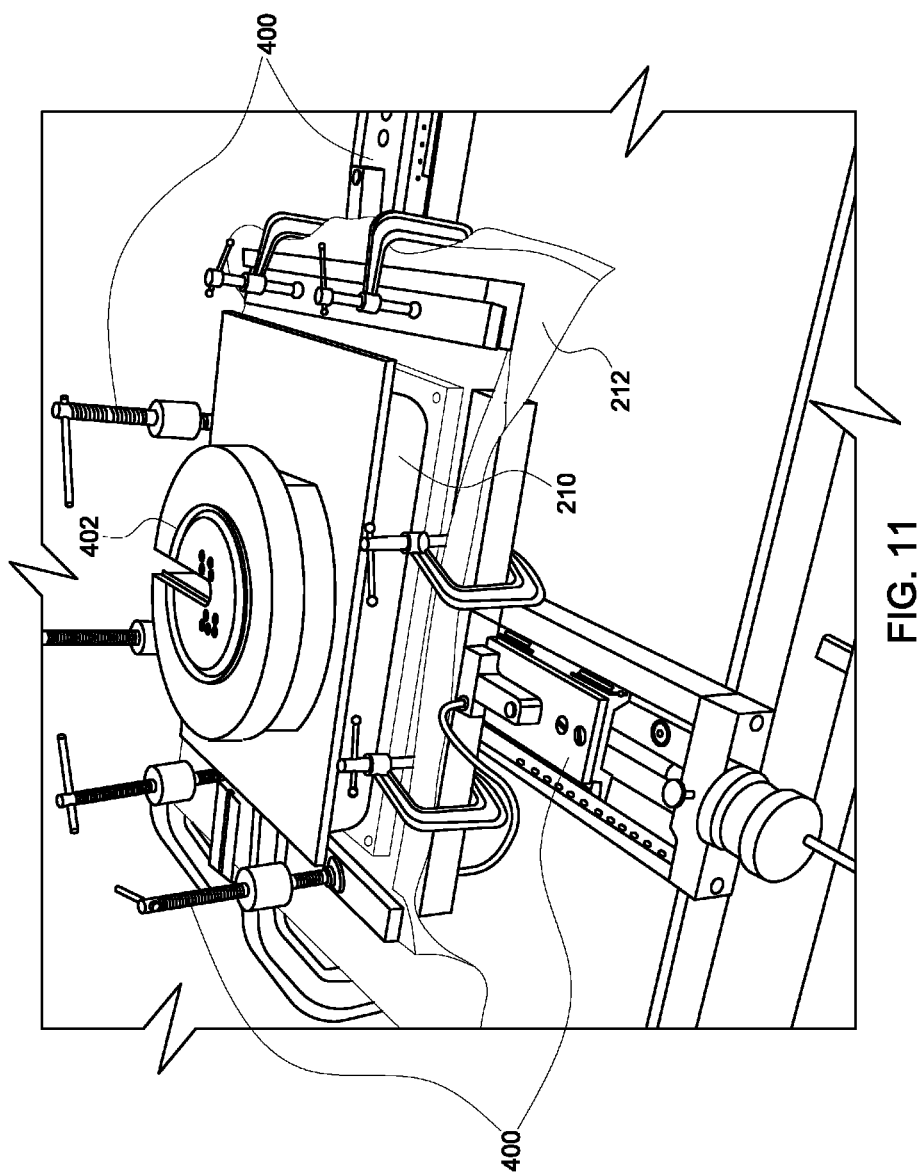
FIG. 11 is a pictorial representation of a paddle assembly under tension and pressure, in accordance with aspects of the present disclosure.

At step 382, the applied mesh 210 a displacement is applied to the mesh with respect to the frame 210. In certain embodiments the applied displacement may allow for the mesh being slack, being taut, or being under tension with respect to the frame 210. For example, in certain embodiments, an applied tension (i.e., a tension 0 or greater) may be applied to the mesh uniformly across the frame 210. In other embodiments the applied tension, if present, may vary such that portions of the mesh 212 over certain regions of the frame 210 are placed under a different tension than other portions of the mesh 212 corresponding to other regions of the frame 210. Turning to FIG. 11, an example of an application of tension is shown where tensioning mechanisms 400 (e.g., linear slides and mesh clamps) are depicted as securing and pulling on the mesh 212 with respect to the frame 210. In the depicted example, the mesh 212 is placed under tension in two different directions, one perpendicular to the other.

Once displaced (such as under tension in certain example), the mesh 212 may be affixed (block 384) to the frame 210, such as by adhesion (e.g., tape, biocompatible epoxy, and so forth) or other affixing mechanisms (e.g., staples or other mechanical fasteners, ultrasonic welding, RF welding, melting or thermal adhesion, and so forth). In the depicted example of FIG. 11, a weight 402 is shown on the assembly, which may help in the setting of an adhesive setting or in otherwise affixing the mesh 212 to the frame.

Figure 12:
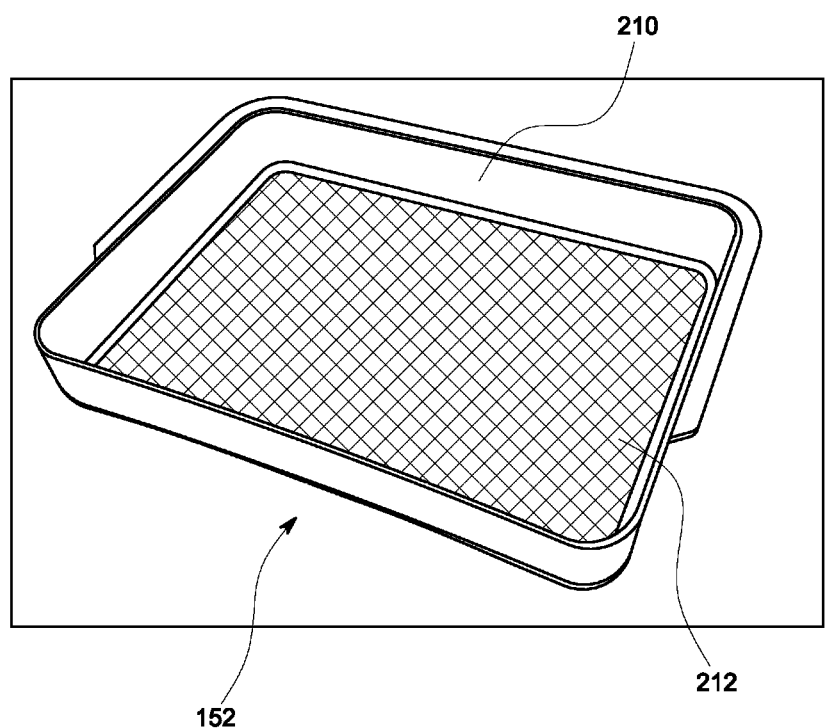
FIG. 12 is a pictorial representation of an assembly non-rigid compression paddle, in accordance with aspects of the present disclosure.

Once the mesh 212 is securely affixed to the frame 210, the mesh compression paddle 152 is manufactured and may be removed from the manufacturing assembly. Additional steps, such as trimming away excess mesh material 212 may also be performed. An example of a manufactured mesh compression paddle 152 is illustrated in FIG. 12.

Alternatively, as noted above, in other embodiments the mesh material may not be under tension but may instead be held loose (i.e., slack) or may be taut but not under a positive tension. In such an embodiment, the compression paddle may be manufactured by cutting the mesh material to a fixed size and mounting the mesh material on the mounting assembly at a fixed location. In one implementation, a pre-determined tension is applied to the mesh material in one or two directions so as to create a uniform initial condition for the mesh material. In this manner, the amount of slack is controlled by releasing the tension, such as by linear slides by a pre-determined distance. The mesh material may then be affixed to the frame with little or no tension and/or with little or no slack.

Technical effects of the invention include the manufacture and use of a non-rigid breast compression paddle, such as a compression paddle having a mesh material forming the primary interface with patient tissue. Technical effects further include an automatic feedback driven approach for compressing breast tissue using a non-rigid paddle, where force measurements derived from the paddle interface are compared against a compression threshold criterion to determine whether additional compression is to be applied.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A breast compression mechanism, comprising:
a breast compression paddle, comprising:
 a frame defining an open region, wherein the frame comprises a patient contacting region that has a curvature corresponding to one or both of breast tissue curvature near a chest wall or an ultrasound probe head curvature;
 a mesh material affixed to the frame over the open region, wherein the mesh material is deformable relative to the frame and is sonolucent; and
 one or more sensors positioned on the frame or mesh material and configured to generate compression measurements when the breast compression paddle is in use;
a mounting assembly comprising a motor controller configured to move the breast compression paddle to achieve a threshold breast compression in response to the compression measurements generated by the one or more sensors during operation.

2. The breast compression paddle of claim 1, wherein the mesh material is at a uniform tension in two perpendicular directions over the open region of the frame.

3. The breast compression paddle of claim 1, wherein the mesh material is at different tensions at over different portion of the open region of the frame.

4. The breast compression paddle of claim 1, wherein the mesh material is not at a uniform tension over the open region of the frame.

5. The breast compression paddle of claim 1, wherein the one or more sensors comprise one or more force measurement devices configured to read a force or a force over a unit area acting upon the mesh material.

6. The breast compression paddle of claim 1, wherein the one or more sensors comprise a conductive wire woven through the mesh material.

7. The breast compression paddle of claim 1, further comprising one or more radio-opaque elements woven into or formed in the mesh material.

8. The breast compression paddle of claim 1, further comprising a sliding engagement formed in the frame.

9. The breast compression paddle of claim 1, wherein all or part of the mesh material and frame are disposable.

10. A breast compression mechanism, comprising:
a breast compression paddle, comprising:
a frame defining an open region, wherein the frame comprises a patient contacting region that has a curvature corresponding to one or both of breast tissue curvature near a chest wall or an ultrasound probe head curvature;
a mesh material affixed to the frame over the open region, wherein the mesh material is sonolucent; and
a conductive wire woven through the mesh material; and
a mounting assembly comprising a motor controller configured to move the breast compression paddle to achieve a threshold breast compression in response to one or both of resistance or inductance measurements generated by the conductive wire during operation.

11. The breast compression paddle of claim 10, wherein the mesh material is at a uniform tension in two perpendicular directions over the open region of the frame.

12. The breast compression paddle of claim 10, wherein the mesh material is at different tensions at over different portion of the open region of the frame.

13. The breast compression paddle of claim 10, wherein the mesh material is not at a uniform tension over the open region of the frame.

14. The breast compression paddle of claim 10, further comprising one or more force measurement devices configured to read a force or a force over a unit area acting upon the mesh material during operation.

15. The breast compression paddle of claim 10, further comprising one or more radio-opaque elements woven into or formed in the mesh material.

16. A breast compression mechanism, comprising:
a breast compression paddle, comprising:
a frame defining an open region, wherein the frame comprises a patient contacting region that has a curvature corresponding to one or both of breast tissue curvature near a chest wall or an ultrasound probe head curvature;
a mesh material affixed to the frame over the open region, wherein the mesh material is sonolucent; and
one or more strain or force sensors positioned on the frame or mesh material and configured to generate force measurements when the breast compression paddle is in use; and
a mounting assembly comprising a motor controller configured to move the breast compression paddle to achieve a threshold breast compression in response to the force measurements generated by the one or more strain or force sensors during operation.

17. The breast compression paddle of claim 16, wherein the mesh material is at a uniform tension in two perpendicular directions over the open region of the frame.

18. The breast compression paddle of claim 16, wherein the mesh material is at different tensions at over different portion of the open region of the frame.

19. The breast compression paddle of claim 16, wherein the mesh material is not at a uniform tension over the open region of the frame.

20. The breast compression paddle of claim 16, wherein the force measurements comprise a force or a force over a unit area acting upon the mesh material during operation.

21. The breast compression paddle of claim 16, further comprising a conductive wire woven through the mesh material.

22. The breast compression mechanism of claim 1, wherein the compression measurements comprise strain or force measured at the breast compression paddle.

23. The breast compression mechanism of claim 1, wherein the compression measurements comprise resistance or impedance measurements in a conductive component of the breast compression paddle.

* * * * *